United States Patent [19]
McFerrin

[11] Patent Number: 5,718,580
[45] Date of Patent: Feb. 17, 1998

[54] VAPOR BLASTER

[76] Inventor: Dennis McFerrin, 1141 S. Foothill Dr., Lakewood, Colo. 80228

[21] Appl. No.: 584,034

[22] Filed: Jan. 11, 1996

Related U.S. Application Data

[63] Continuation-in-part of Ser. No. 372,073, Jan. 12, 1995, abandoned.

[51] Int. Cl.[6] ............................................. A61C 17/00
[52] U.S. Cl. .................................... 433/80; 433/100; 239/415
[58] Field of Search ............................... 433/80, 88, 99, 433/100, 98; 239/415

[56] References Cited

U.S. PATENT DOCUMENTS

| | | | |
|---|---|---|---|
| 2,717,806 | 9/1955 | Dale | 239/415 |
| 3,137,297 | 6/1964 | Maurer et al. | 433/80 |
| 3,235,186 | 2/1966 | Boyce | 239/415 |
| 3,658,255 | 4/1972 | Beall, Jr. | 239/415 |
| 3,698,088 | 10/1972 | Austin, Jr. | 433/80 |
| 3,727,310 | 4/1973 | Baker . | |
| 4,629,425 | 12/1986 | Detsch | 433/80 |
| 4,872,837 | 10/1989 | Issalene et al. . | |
| 4,936,511 | 6/1990 | Johnson et al. . | |
| 4,975,054 | 12/1990 | Esrock . | |
| 5,049,071 | 9/1991 | Davis et al. . | |
| 5,067,899 | 11/1991 | Paschal . | |
| 5,082,443 | 1/1992 | Löhn . | |
| 5,273,428 | 12/1993 | Fischer | 433/80 |
| 5,350,299 | 9/1994 | Gallant | 433/88 |
| 5,360,338 | 11/1994 | Waggoner | 433/80 |

*Primary Examiner*—Cary E. O'Connor
*Attorney, Agent, or Firm*—Rick Martin

[57] ABSTRACT

A hand held blow gun is designed to help dental lab technology wash, rinse, and dry a prosthesis using one hand. High pressure air (100 p.s.i.) is needed to clean the work piece. Next a wash and finally an air dry process is needed. The vapor blaster is a one piece hand held device having a single thumb actuated lever to progressively depress first an air valve and then a water valve. The invention is powered by a high pressure gas source connected to a high pressure regulator. The high pressure regulator is connected to the hand held blow gun and to a second low pressure regulator connected to the remote second water bottle. An optional second water bottle is shown to select a cleaning solution cycle with T switches.

8 Claims, 5 Drawing Sheets

VAPOR BLASTER

CROSS REFERENCE PATENTS

This application is a continuation-in-part of application Ser. No. 08/372,073 filed on Jan. 12, 1995, now abandoned.

FIELD OF INVENTION

The present invention relates to an improved high pressure air blow gun having an auxiliary water bottle to provide dental lab technicians one-handed operation of a cleaning tool.

BACKGROUND OF THE INVENTION

A need exists to improve the efficiency of dental lab technicians in the fabrication of dental prosthesis. Presently, it takes a two handed operation to spray wash a prosthesis, then rinse it, then dry it. Other industries have the same unmet need. These industries include electronics, small precision equipment, and automotive repair.

In the process of fabricating a dental bridge, crown, or denture the piece needs to be ground, thus creating dust and debris. This dust and debris must be cleaned off in between various finishing operations. Thus, time can be saved if the dental lab technician can hold the piece in one hand and first wash, then rinse, and finally dry the prosthesis using a convenient hand tool in the other hand.

Conventional lab equipment includes a separate high pressure air hose and a sink. The closest known prior art includes oral syringes which dentists use inside the mouth. The following oral syringes have output pressures which are too low for use in a lab sink.

U.S. Pat. No. 3,727,310 (1973) to Baker discloses an oral dental syringe having a handy switch to control water, air, water-air mixture, or vacuum from the syringe. No pressure range is described. The use is for dental procedures.

U.S. Pat. No. 4,872,837 (1989) to Issalene et al. discloses an oral dental instrument for lighting, washing with liquid, washing with sprayed liquid, drying with air, and aspirating.

U.S. Pat. No. 4,936,511 (1990) to Johnson et al. discloses a spray gun for applying high viscosity liquids with air pressure. A disposable liquid handling portion allows applying two part epoxies.

U.S. Pat. No. 4,975,054 (1990) to Esrock discloses a dental syringe having an air stream, water stream, or air-water stream. A quick release nozzle is taught.

U.S. Pat. No. 5,049,071 (1991) to Davis et al. discloses a dental syringe with a disposable nozzle. A plurality of air passageways surround the water passageway.

U.S. Pat. No. 5,067,899 (1991) to Paschal discloses an oral syringe having a splashback prevention plate.

U.S. Pat. No. 5,082,443 (1992) to Löhn discloses an oral syringe having a light and a thin cross-section.

The present invention provides a single thumb actuated lever which progressively releases first only air, then air and water, then only water. The one piece hand gun is connected to the air supply and a water tank.

SUMMARY OF THE INVENTION

The main object of the present invention is to provide a hand gun that can be held in one hand and progressively supply a blast of air then air and water.

Another object of the present invention is to provide a remote second tank for holding a cleaning solution. A "T" valve allows the user to select either the water or the cleaning solutions to be injected into the vapor blaster.

Another object of the present invention is to provide a brush at the nozzle of the vapor blaster to facilitate debris removal from the workpiece.

Other objects of this invention will appear from the following description and appended claims, reference being had to the accompanying drawings forming a part of this specification wherein like reference characters designate corresponding parts in the several views.

The concept of the vapor blaster is a hand-held device which is connected to an air line and a remote tank or bottle which would be used to provide air and an air/water or an air/cleaning solution mixture for use in cleaning off various dental prosthesis while they are being manufactured. The vapor blaster consists of a plastic hand gun which has separate valves for the air and air/fluid mixtures. By pressing the lever progressively down, a stream of air and air/liquid can be directed at the item to be cleaned. The hand gun is connected by plastic tubing and air lines to air outlets and a remote storage tank for the liquid/air solution.

By manipulation of the lever, with the inclusion of a third chamber for accommodation of a cleaning/air solution, an item which is being worked can be washed, rinsed, and dried. The optional brush at the nozzle of the vaper blaster facilitates debris removal from the workpiece.

The system which comprises the vapor blaster consists of a remote tank to hold the solution, consisting of a plastic container which has been capped on top, an air regulator assembly, air gauge, manual air release valve on the inlet side of the air regulator assembly, and plastic hoses.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
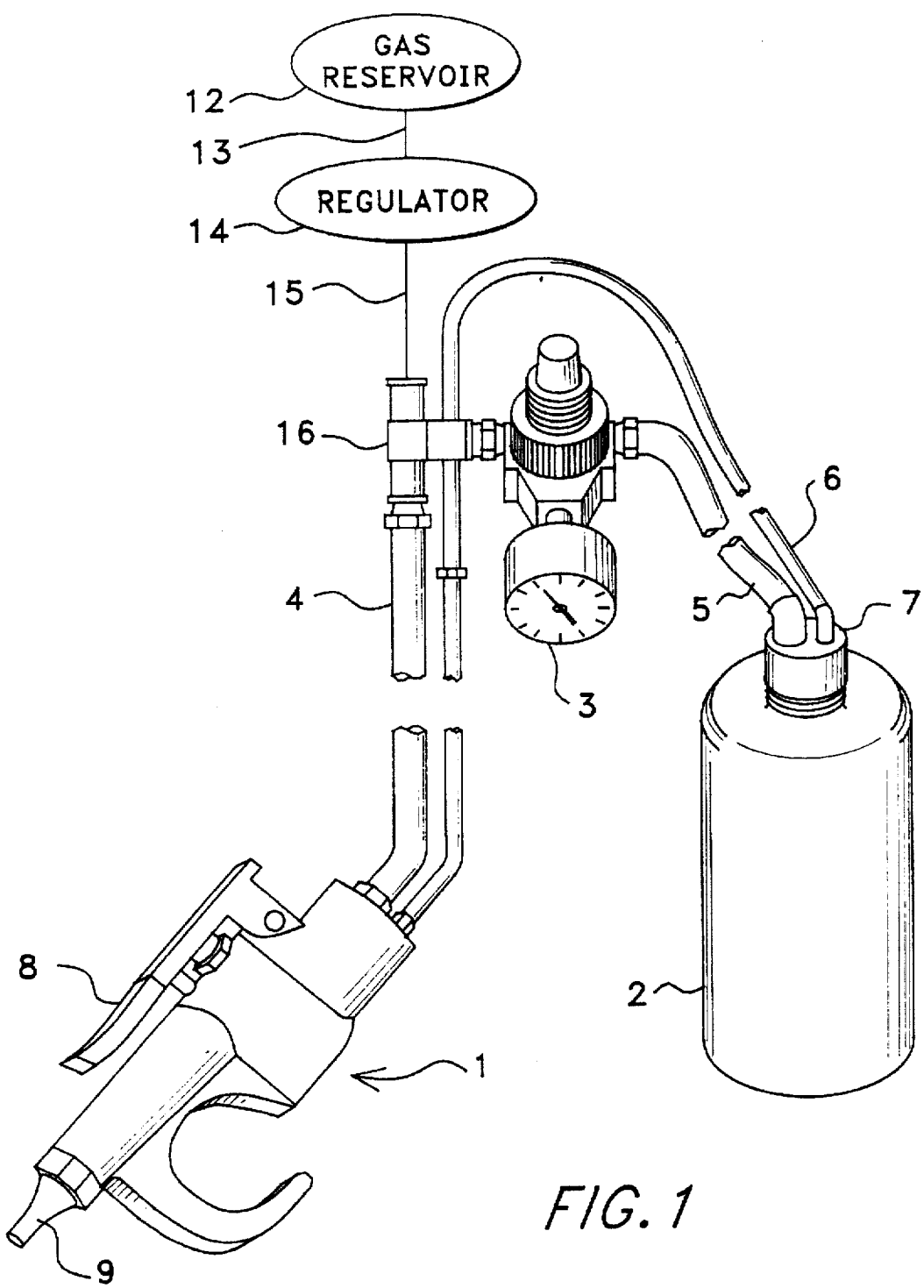
FIG. 1 is a top perspective view of the components of the preferred embodiment.

Referring first to FIG. 1 The high pressure gas reservoir 12 transmits high pressure gas through steel pipe 13 to the high pressure regulator 14. The high pressure regulator 14 reduces the pressure of the gas to 100 psi nominally. The gas passes through pipe 15 to the "T" 16. The hand gun 1 receives nominally 100 p.s.i. of air from the air inlet indicated by the arrow as transmitted by the flexible tube 4. The air regulator 3 controls a safe pressure (nominally 3 p.s.i.) to remote bottle 2 via flexible tube 5. The cap 7 provides removable attachment of flexible tube 5 and water outlet tube 6. A thumb actuated lever 8 allows progressive discharge of air and air water combined from the nozzle 9.

The present invention allows use without the need for a piped water source. This reduces the expense of the device. It also allows the user the ease of use with wide reach thereby affording greater convenience to the user.

Figure 2:
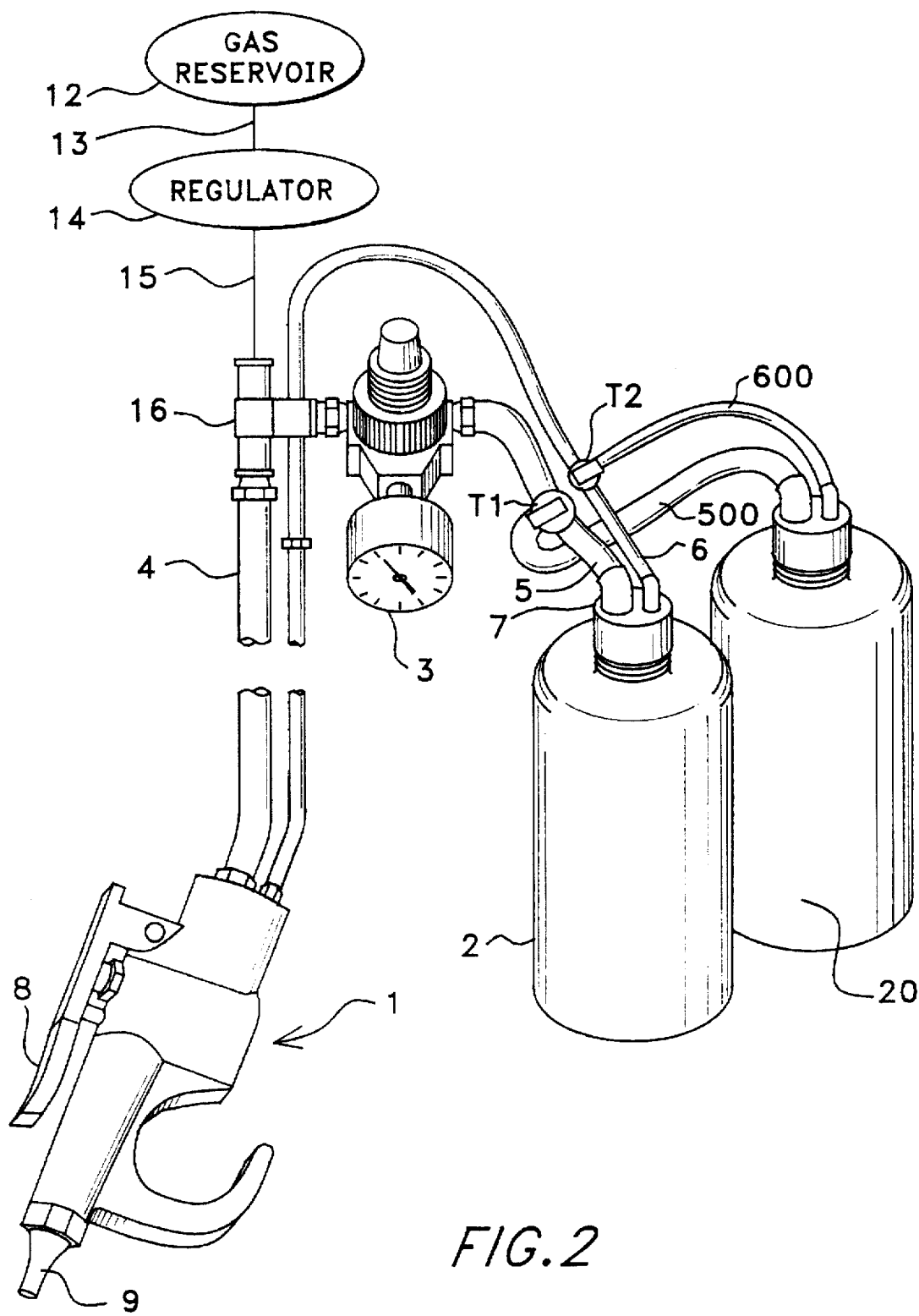
FIG. 2 is a top perspective view of the alternate embodiment having a cleaning solution tank.

Referring next to FIG. 2 the alternate embodiment having a selectable cleaning solution bottle is shown.

In the alternate embodiment shown in FIG. 2 a second remote bottle 20 contains a washing solution. "T" connections $T_1$, $T_2$ enable the user to switch to remote bottle 20. Flexible tubes 500, 600 are analogous to flexible tubes 5, 6.

Figure 3:
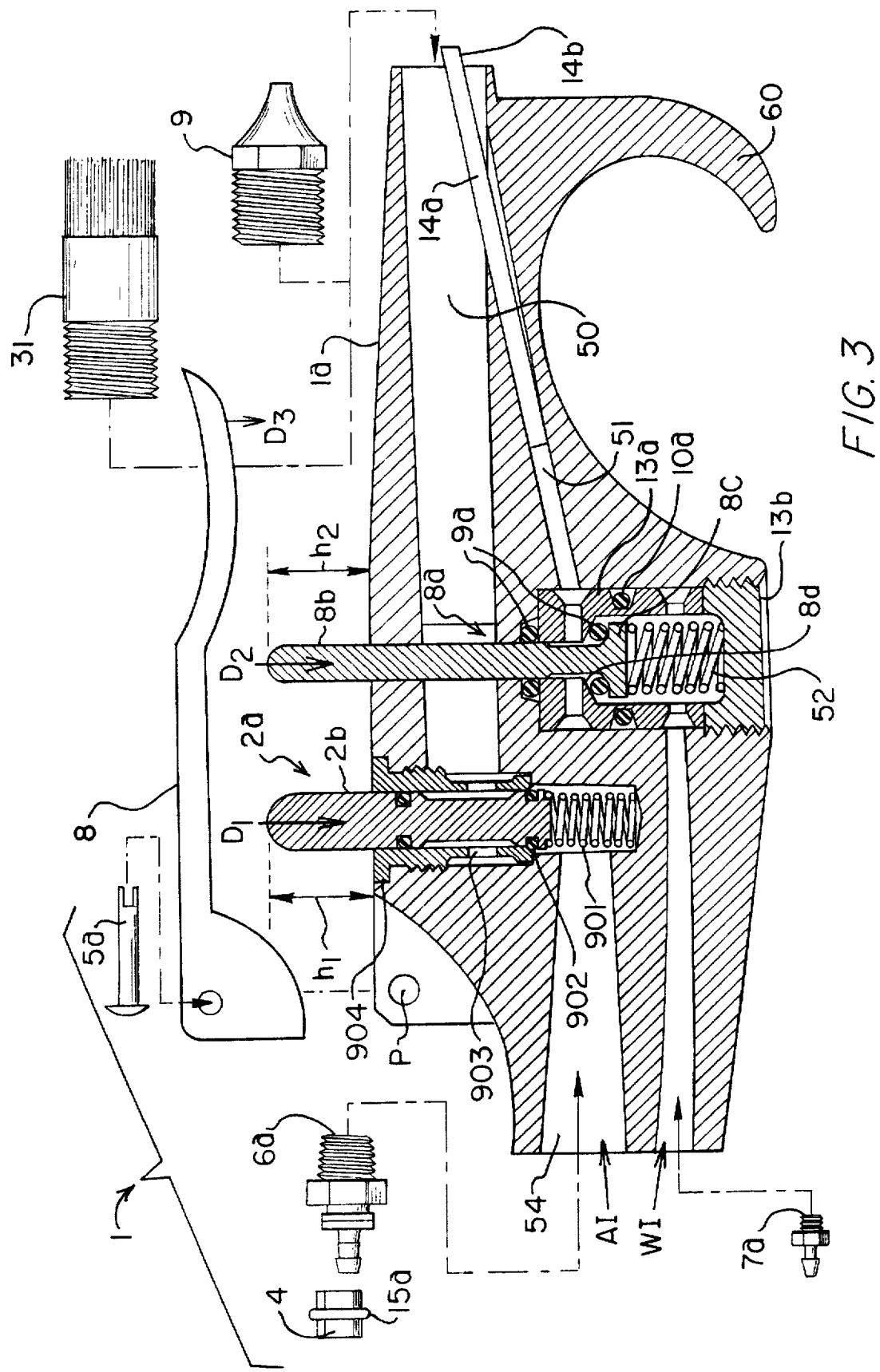
FIG. 3 is a longitudinal sectional view partially exploded of the hand gun shown in FIGS. 1, 2, with the addition of an alternate embodiment nozzle shown in FIG. 6.

Referring next to FIG. 3 the hand gun 1 is shown in a partially exploded view. The body 1a is preferably produced in a one piece plastic mold. The pressurized air connects to inlet AI. The water connects to inlet WI. The air is normally blocked by valve 2a. By depressing the plunger 2b the air flows down channels 54, 50 and out the nozzle 9. A simple plunger and channel arrangement inside valve 2a provides a direct relationship between the plunger 2b travel in direction $D_1$ and the air flow into channel 50.

Spring 901 returns the plunger 2b to the "OFF" position shown. In the "OPEN" position (not shown) the air travels around O-ring 902 and out the valve jacket orifice 903. The valve jacket 904 screws into the body 1a.

The water is normally blocked by valve 8a. By depressing the plunger 8b the water flows out channel 51 and out the outlet tube 14a whose tip 14b is mounted inside the nozzle 9. The valve arrangement consists of a valve stem 8c, a valve seat 8d, O-rings 9a, a valve seat O-ring 10a, and a spring 52. Valve jacket 31a is retained in vapor blaster 1 by threaded plug 13b. A direct relationship is created between the plunger 8b travel in direction $D_2$ and the water flow into channel 51.

Figure 6:
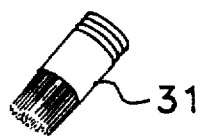
FIG. 6 is a perspective view of an alternate embodiment nozzle fixture haveing an integral brush.

The lever 8 pivots about point P. Rivet 5a holds the lever arm 8 in place. As lever 8 is depressed in direction $D_3$ it first depresses plunger 2b because height h1 is greater than height h2 of plunger 8b. After lever 8 depresses plunger 2b, it then depresses plunger 8b. Thus, the output stream from nozzle 9 starts as air then changes to an air water mixture. Brush 31 is threadably attached to nozzle 9 as shown in FIGS. 3 and 6.

Optional brush 31 is used to scrub and clean the surface of interest. The flow of air and or water loosens debris which the removal of is further encouraged by the brush 31.

The flexible tube 4 attaches to nipple 6a by means of a hose clamp 15a. The flexible tube 6 attaches to nipple 7a.

The hook 60 is used to hang the device on a drawer, wall, and the like.

Figure 4:
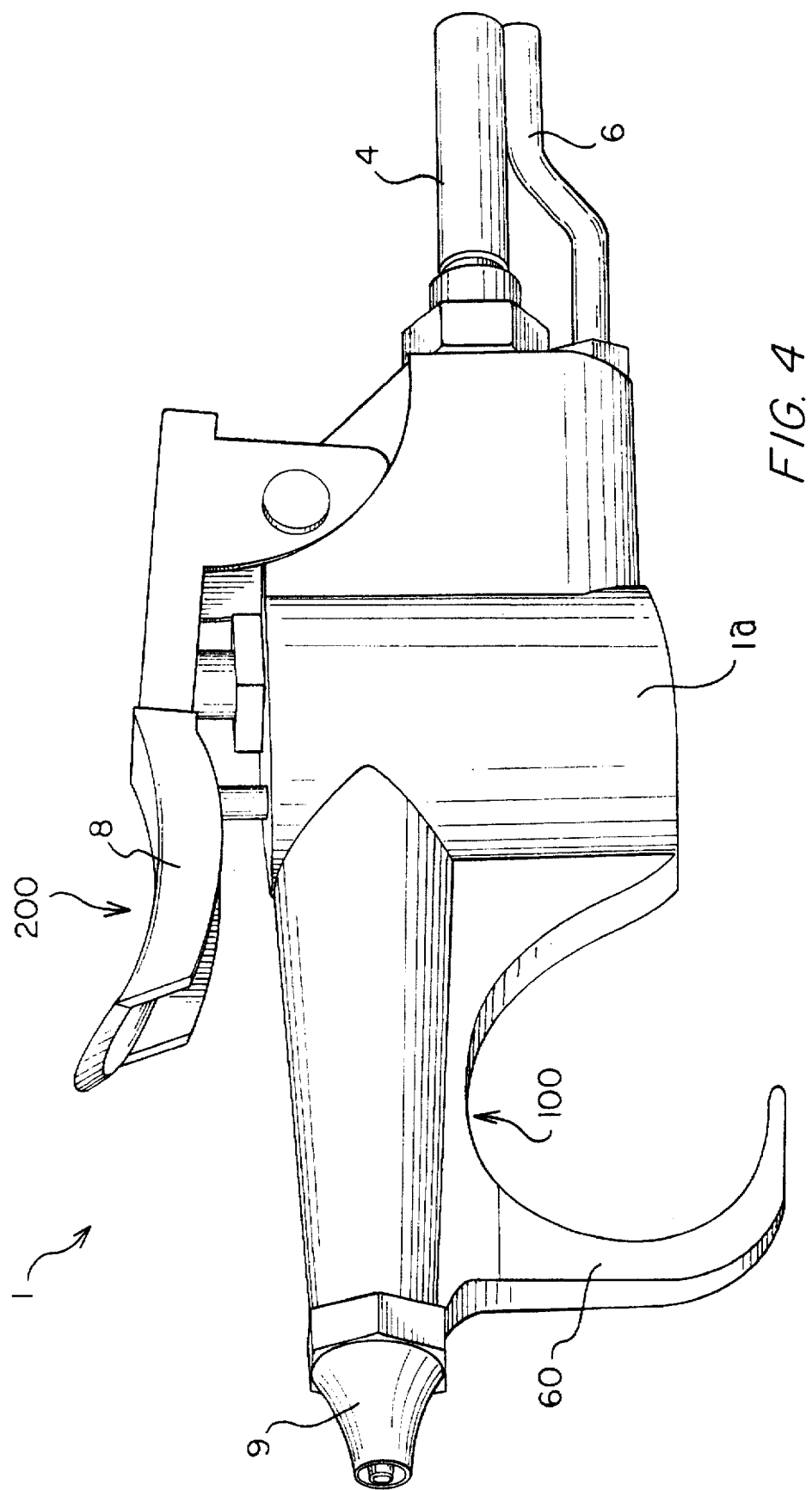
FIG. 4 is a left side perspective view of the hand gun shown in FIGS. 1, 2.
Figure 5:
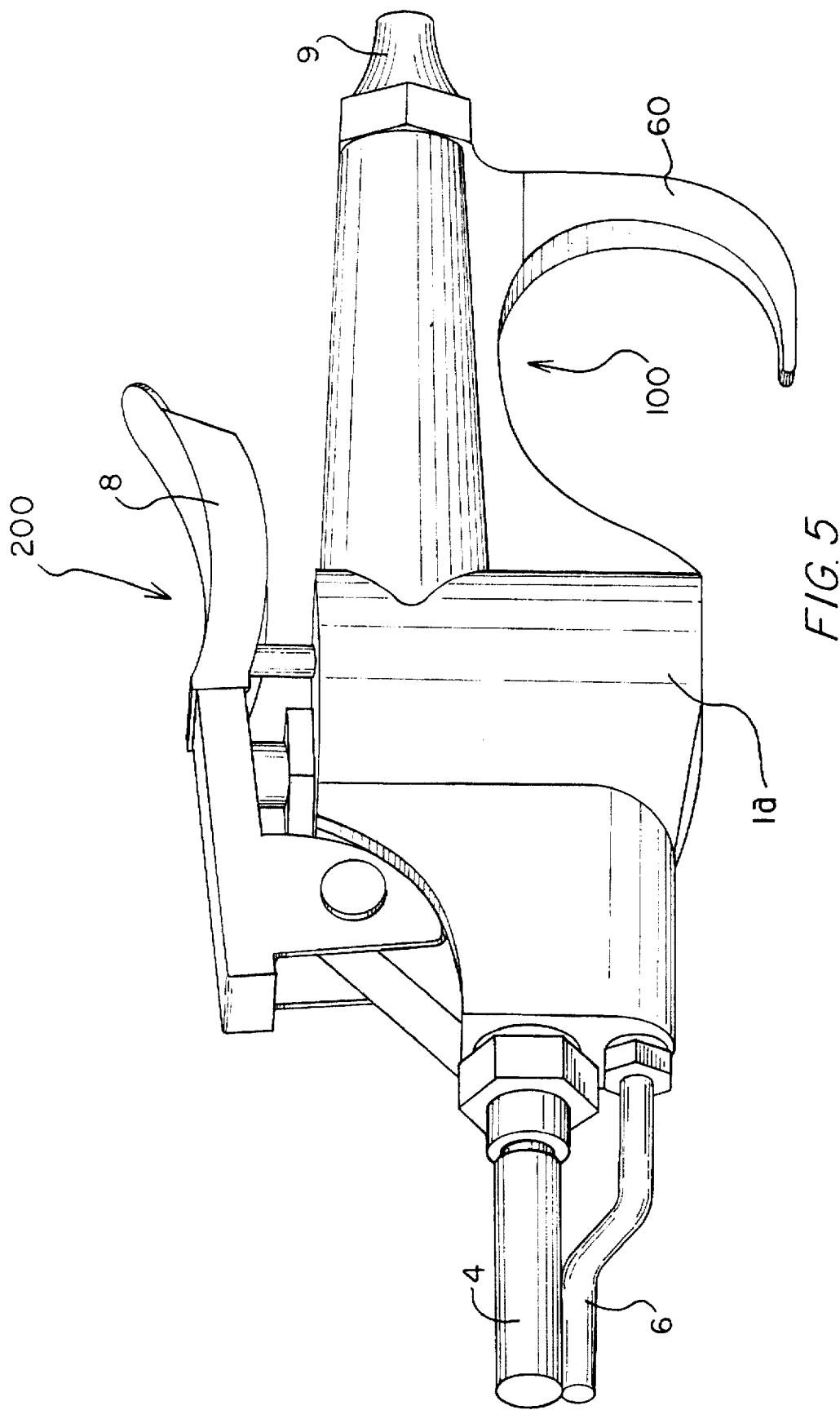
FIG. 5 is a right side perspective view of the hand gun shown in FIGS. 1, 2.

Referring to FIGS. 4, 5 the thumb (not shown) depresses the lever 8 at 200. The four digit fingers grip the body 1a at 100.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A vapor blaster comprising:

a high pressure air supply;

a fluid container having a low pressure source;

a one hand holdable body having an inlet for the air supply and an inlet for the fluid container;

valving means inside the body for the air supply to provide no air and progressively more air;

valving means inside the body for the water supply to provide no fluid, progressively more fluid, and a maximal fluid flow;

a nozzle means functioning to transport an output stream;

a switch means to progressively provide an output air stream and an air water stream from the nozzle means; and said low pressure source further comprises a regulator supplied by the high pressure air supply.

2. The vapor blaster of claim 1, wherein said valving means for the air supply further comprises a spring loaded plunger having a channel controllably moved progressively in and out of alignment with an air inlet channel.

3. The vapor blaster of claim 2, wherein said valving means for the water supply further comprises a spring loaded plunger having a valve stem movably engaged with a valve seat.

4. The vapor blaster of claim 3, wherein said switch means further comprises a finger actuated lever which first engages the air supply plunger and then engages the water supply plunger.

5. The vapor blaster of claim 1, further comprising a cleaning solution supply and a switching means to selectively switch either the water supply or the cleaning solution supply into the body.

6. The hand gun of claim 1, wherein the valving means for controlling the high pressure air source further comprises an air depressable plunger, and the valving means for controlling the water source further comprises a water depressable plunger.

7. The hand gun of claim 1, wherein said switch means further comprises a lever means functioning to first depress the air depressable plunger and next the water depressable plunger.

8. A vapor blaster comprising:

a high pressure air supply;

a fluid container having a low pressure source;

a one hand holdable body having an inlet for the air supply and an inlet for the fluid container;

an air supply valve inside the body having a variable output ranging from no air to progressively more air;

a water supply valve inside the body having a variable output ranging from no fluid, to a maximal fluid flow;

a nozzle to transport an output stream;

a switch to progressively provide an output air stream and an air water stream from the nozzle means; and said low pressure source further comprises a regulator supplied by the high pressure air supply.

* * * * *